United States Patent [19]

Cushing et al.

[11] Patent Number: 5,759,864
[45] Date of Patent: Jun. 2, 1998

[54] METHODS FOR REDUCING BACKGROUND BINDING IN ANTIBODY PREPARATIONS

[75] Inventors: Susan Cushing, Van Nuys; Alda Vidrich, Pacific Palisades, both of Calif.

[73] Assignee: Cedars Sinai Medical Center, Los Angeles, Calif.

[21] Appl. No.: 494,136

[22] Filed: Jun. 23, 1995

[51] Int. Cl.6 .................. C01N 33/53; C01N 33/573; G07K 16/00
[52] U.S. Cl. .................. 436/547; 436/825; 435/7.2; 435/7.21; 435/7.25; 435/40.51; 435/40.52; 435/962; 530/388.26; 530/389.1
[58] Field of Search .................. 435/7.2, 962, 7.1, 435/7.21, 7.25, 40.51, 40.52; 530/391.1, 389.1, 390.1, 390.5, 388.26; 436/547, 825

[56] References Cited

U.S. PATENT DOCUMENTS

| | | | |
|---|---|---|---|
| 3,697,645 | 10/1972 | Meier et al. | 424/85 |
| 4,604,235 | 8/1986 | Flashner | 530/417 |
| 4,683,295 | 7/1987 | Carson | 530/391 |
| 4,722,896 | 2/1988 | Kadish | 435/68 |
| 4,841,024 | 6/1989 | Nathans et al. | 530/413 |
| 4,849,352 | 7/1989 | Sullivan et al. | 435/69 |
| 4,933,435 | 6/1990 | Ngo | 530/413 |
| 5,059,518 | 10/1991 | Kortright et al. | 435/6 |
| 5,110,913 | 5/1992 | Coan et al. | 530/388.23 |
| 5,151,504 | 9/1992 | Croze | 530/413 |
| 5,308,753 | 5/1994 | Dorward et al. | 435/7.32 |
| 5,312,744 | 5/1994 | Shibata | 435/174 |
| 5,460,797 | 10/1995 | Ryan | 435/40.5 |
| 5,585,356 | 12/1996 | Liotta et al. | 514/17 |

FOREIGN PATENT DOCUMENTS 0 441 469 A1  8/1991  European Pat. Off.
WO 94/15950  7/1994  WIPO.

OTHER PUBLICATIONS

Mittal, et al., *Virus Res.* vol. 28, No. 1, pp. 67–90, 1993. Abstract only.

Adlercreutz, *Enzyme Microb Technol*, vol. 13, No. 1, pp. 9–14, 1991. Abstract only.

Harlow, et al., "Antibodies—A Laboratory Manual," Cold Spring Harbor Laboratory (1988), at 364, 632–33.

Levitt, D. et al., *Journal of Immunological Methods*, "Methanol fixation permits flow cytometric analysis of immunofluorescent stained intracellular antigens," 96(2):223–237 (11 Feb. 1987).

Fiskum, G. et al., *Proceedings of the National Academy of Sciences of the USA*, "The cytoskeleton of digitonintreated rat hepatocytes," 77(6):3430–3434 (Jun. 1980).

*Primary Examiner*—Toni R. Scheiner
*Attorney, Agent, or Firm*—Pretty, Schroeder & Poplawski

[57] ABSTRACT

In accordance with the present invention, there are provided novel methods and reagents for reducing background binding in antibody preparations having an unwanted affinity for intracellular protein(s). The invention method comprises treating an antibody preparation with permeabilized cells, then separating the antibody preparation from the permeabilized cells. The reagents are useful for reducing the level of background binding in antibody preparations. Also provided are antibody preparations that are substantially free of background binding.

35 Claims, No Drawings

METHODS FOR REDUCING BACKGROUND BINDING IN ANTIBODY PREPARATIONS

FIELD OF THE INVENTION

The present invention relates to methods and reagents for reducing the level of background binding in antibody preparations having unwanted affinity for intracellular protein(s). The invention also relates to antibody preparations that are substantially free of background binding.

BACKGROUND OF THE INVENTION

Immunological applications that demand specific binding between antibody and antigen may be compromised by the presence of high concentrations of other macromolecules. For example, a good polyclonal serum will contain multiple antibodies directed against different epitopes on an antigen. In addition to specific, desirable antibodies, polyclonal sera generally also contain relatively high concentrations of irrelevant antibodies of unknown specificity. These will include the entire repertoire of antibodies in the animal when the serum was collected. These antibodies create troublesome problems in applications such as, for example, efforts to detect specific antigen/antibody binding on cultured cells and tissue sections. The presence of unwanted binding by antibodies of unknown specificity can make it difficult or impossible to detect specific binding by the antibody of interest. This unwanted binding is referred to as "background."

For example, background binding is very high in polyclonal antibodies raised in rabbits against the reporter gene product, firefly luciferase. Reporter genes are routinely used in cell biology for the study of gene function and related cellular events. The gene encoding firefly luciferase has proven to be highly effective for this purpose. This enzyme catalyzes the oxidation of beetle luciferin with the concomitant production of a photon. The firefly luciferase gene is a widely used reporter gene because the luciferase protein: (1) produces light with the highest quantum efficiency known for any chemiluminescent reaction; (2) remains intracellular; and (3) requires no post-translational processing for enzyme activity and can therefore function immediately upon translation. At this time, the only method for reliable detection of luciferase is to monitor the light produced by the enzyme. While this type of assay provides information about gene function and relative rates of transfection, it provides no information about specific transfection efficiency, which is critical information in many instances. An antibody preparation free from background-creating antibodies, that could reliably and specifically detect the gene product luciferase in a wide variety of species and tissues, could provide this information. At this time, no such antibody preparation exists.

Methods for removing background-creating contaminants from antibody preparations typically are based on differences in physicochemical attributes such as electric charge, size and shape, hydrophobicity, and/or binding specificity. Most purification methods are based on chromatographic separations that are designed to produce specific antibodies. Although effective, the development of these methods is often very time consuming and hence, costly, because, for example, they require the empirical development of the requisite conditions for achieving the separation of product and contaminant antibodies.

For example, ion exchange chromatography is used to separate contaminants from antibody preparations based on differences in charge. The electric charge of proteins and antibodies is conferred by free side chain groups present on arginine, aspartic acid, cysteine, glutamic acid, histidine, lysine, and tyrosine. The net charge is low but sufficient to enable interaction with the charged side groups of ion exchange resins. Resolution of antibodies and contaminants is based on differences in charge and chromatography pH. Operation at pHs above or below the isoelectric point may enable acceptable separation of product from background antibodies. In this method, a protein-containing solution is passed over or through appropriate ion exchange material at a solution pH which facilitates binding of the desired protein. This is commonly followed by a washing step and an elution step at a different ionic strength or pH, which facilitates the release of the protein. In general, altering the pH of a protein towards its isoelectric point causes it to lose net charge and elute from an ion exchanger. One drawback of using ion exchange chromatography to purify antibodies is that the pH required for distinguishing between product and contaminant charge may lie outside the stable range of the antibody. Moreover, a key disadvantage of ion exchange chromatography is that the separation process may be very slow because of slow intraparticle diffusion through traditionally used porous supports. See, for example, Papoutsakis et al., *Recombinant DNA Technology and Applications*, 357 (New York 1991).

Affinity chromatography is a separation technique based on the highly selective binding exhibited by many biological molecules to ligands. As the product stream flows past beads containing immobilized ligand, the ligand reacts specifically with the product, which is retained on the column. The column is then washed to remove nonspecifically adsorbed proteins. After washing, conditions in the column are changed (e.g., temperature, pH, or ionic strength) to encourage elution of the product from the column. Although effective, affinity chromatography is a very time consuming method to develop. This is because the appropriate conditions for separation must be identified from a number of variables (e.g., temperature, pH, ionic strength of mobile phase, solid phase composition, and mobile phase composition). In addition, the high cost of the immobilized ligand makes affinity chromatography better suited for relatively small scale final stage purification processing.

Proteins and antibodies can also be purified by selective precipitation of either product or contaminant antibodies. This is generally accomplished by salting out with ammonium sulfate, polyethylene glycol (PEG), or specific precipitants, such as calcium ions. However, a major limitation of the precipitation method is that purification is only possible when the product and contaminant exhibit different precipitation behavior within the same system. Determination of an appropriate precipitation system depends on variables such as solution temperature, pH, composition, ionic strength, dielectric constant, the precipitant selected, etc. Even when separation is possible, in many cases, the protein and antibody yields are less than desired.

Accordingly, a need clearly exists for cost effective methods for reducing the level of background binding in antibody preparations. A need also exists for antibody preparations that are substantially free of background binding.

BRIEF DESCRIPTION OF THE INVENTION

In accordance with the present invention, we have developed a method for reducing the level of background binding in antibody preparations having unwanted affinity for intracellular protein(s). The invention method comprises treating the antibody preparation with permeabilized cells, then separating the treated antibody preparation from the permeabilized cells.

In accordance with another embodiment of the present invention, we have developed an anti-luciferase polyclonal composition that is substantially free of background binding.

In yet another embodiment of the present invention, there is provided a reagent for removing background binding from antibody preparations having unwanted affinity for intracellular proteins.

DETAILED DESCRIPTION OF THE INVENTION

In accordance with the present invention, a method for reducing background binding in antibody preparations having unwanted affinity for intracellular protein(s) is provided. The invention method comprises (i) treating an antibody preparation with permeabilized cells to produce a treated antibody preparation,
   wherein said permeabilized cells are prepared by contacting whole cells with a suitable permeabilizing agent,
   wherein said permeabilizing agent comprises an agent selected from the group consisting of alcohols and aqueous alcohols, aldehydes and aqueous aldehydes, aqueous alcohols, aldehydes and aqueous aldehydes, ketones and aqueous ketones, nonionic surfactants and aqueous media containing nonionic surfactants, and combinations of any two or more thereof, provided, however, that the permeabilizing agent is not neat acetone, then (ii) separating the treated antibody preparation from the permeabilized cells.

The term "background binding" refers herein to the occurrence of unwanted antibody binding from an antibody preparation containing an antibody of interest. The unwanted binding is typically caused by antibody binding to intracellular proteins. Unwanted antibody binding interferes with the detection and measurement of binding signals attributable to the antibody of interest. As used herein, the term "signal" refers to a positive indicator of antibody binding. Exemplary signals include the visual detection of a change in color, absorbance, reflectance, fluorescence, and other like signals. These indicators are used in methodologies for detecting the presence of particular antibodies and antigens. Such methodologies include cell staining techniques, ELISA assays, and other methods and techniques that are well known in the art. For example, in antibody binding experiments employing cells, background binding is characterized by prevalent and seemingly indiscriminate binding signals. Thus, the presence of background binding makes it virtually impossible to detect specific binding signals of the antibody of interest.

As used herein, "antibody preparation" refers to a population of antibodies that is heterogeneous with respect to the character of epitopes available for binding. Exemplary antibody preparations for use in the practice of the present invention include polyclonal antibodies and mixtures of polyclonal antibodies. The term "polyclonal antibodies" is used herein to refer to antibodies produced in the normal immune response to an antigen that includes a number of closely related but non-identical proteins. The variation reflects the fact that they are formed by a number of lymphocytes.

As used herein, the term "affinity" refers to a specific attraction between molecules, such as for example, the binding of specific antibodies to specific epitopes on an antigenic molecule. In antibody preparations, unwanted affinity for intracellular proteins is typically caused by the presence of background binding antibodies.

Any animal used to make polyclonal antibodies can yield undesirable antibodies that have high background reactivity. Generally, any polyclonal raised against a desired antigenic component can potentially contain unwanted background binding antibodies. Certain animals are likely to generate background, which manifests itself as ubiquitous binding of unwanted antibodies to intracellular proteins. For example, polyclonal antibodies that are raised in rabbit, rat, mouse, sheep, goat, chicken, horse, donkey, and guinea pig appear likely to contain antibodies that are specific to cytoskeletal proteins.

As used herein, the term "permeabilized cells" refers to cells that have cell membranes that have been rendered permeable to antibodies. The term "permeabilizing agent," as used herein, refers to an agent that renders cell membranes permeable to antibodies, provided, however, that "permeabilizing agent" does not refer to neat acetone. As contemplated in the practice of the present invention, permeabilized cells are prepared by contacting whole cells with a suitable permeabilizing agent.

Exemplary permeabilizing agents include alcohols and aqueous alcohols, aldehydes and aqueous aldehydes, ketones and aqueous ketones (excluding neat acetone), nonionic surfactants and aqueous media containing nonionic surfactants, and combinations of any two or more thereof. Suitable alcohols include methanol, ethanol, and the like, and mixtures thereof. Suitable aldehydes include formalin, glutaraldehyde, and the like, and mixtures thereof. Suitable ketones include acetone, methyl ethyl ketone, 3-pentanone, and the like, and mixtures thereof. Suitable non-ionic surfactants include polyethoxylated alcohols, polyethoxylated alkylphenols, polyethoxylated fatty acids, polyalkylene oxide block copolymers, carboxylic acid esters, carboxylic amides, and the like, and combinations of any two or more thereof. Exemplary non-ionic surfactants include Triton® (Rohm and Haas Co., Philadelphia, Pa.), Tween® (ICI Americas Inc., Wilmington, Del.), and Tergitol® NP40 (Union Carbide Corp., Danbury, Conn.).

The permeabilizing agents contemplated by the present invention are typically used under conditions that are sufficient to render cell membranes permeable to antibodies but not sufficient to substantially denature intracellular proteins. As used herein, the term "denature" refers to a change in the structural configuration of a protein so that a denatured protein has fewer epitopes available for binding.

Suitable permeabilized cells include those prepared from hepatocytes, epithelial cells, mesenchymal cells, endothelial cells, muscle cells, neural cells, and the like, as well as combinations of any two or more thereof. As contemplated in the practice of the present invention, exemplary whole cells for permeabilization can be obtained from most any vertebrate species, such as, for example, pig, rabbit, mouse, human, monkey, and the like.

The choice of suitable cell type and species for permeabilization will depend on the particular antibody preparation being used. If the antibody preparation is polyclonal, the antigen against which the polyclonal is raised preferably is not endogenous to the cell type and species selected for permeabilization. For example, a particularly suitable polyclonal and cell type combination is anti-luciferase and pig hepatocytes because the antigen, luciferase, is not endogenous to mammalian hepatocytes.

As used herein, the term "treating" refers to the exposure of an antibody preparation containing unwanted background binding antibodies to permeabilized cells. The antibody preparation can be treated with permeabilized cells either with or without agitation. For example, the permeabilized cells can be left to stand in the antibody preparation without agitation. Preferably, the antibody preparation and permeabilized cells are gently agitated to increase the transport of antibodies into the cells, which thus, increases the binding rate of unwanted antibodies to intracellular proteins. The permeabilized cells can be gently agitated in the antibody preparation by shaking, stirring, rocking, and other mechanical mixing methods that are well known in the art.

The term "contacting," as used herein, refers to the exposure of whole cells to a suitable permeabilizing agent under conditions that are sufficient to render the cells permeables to antibodies. As contemplated in the practice of the present invention, whole cells can be contacted with suitable permeabilizing agent either with or without agitation. For example, whole cells can be left to stand in permeabilizing agent without agitation. Alternatively, whole cells can be gently agitated in permeabilizing agent by shaking, stirring, rocking, or other mechanical mixing methods that are well known to those skilled in the art.

Whole cells are typically permeabilized by contacting with a suitable quantity of suitable permeabilizing agent for a period ranging from about 1 minute to about 36 hours at a temperature ranging from about $-20°$ C. to about $22°$ C. However, temperatures may be higher or lower depending on a variety of factors, such as the duration of contact with the permeabilizing agent, the presence or absence of agitation, etc. For most systems, permeabilization occurs by contacting whole cells with suitable permeabilizing agent for a period ranging from about 30 minutes to about 24 hours at a temperature ranging from about $-20°$C. to about $22°$ C. Preferably, whole cells are permeabilized by contacting with suitable permeabilizing agent for a period ranging from about 15 minutes to about 30 minutes at a temperature ranging from about $-20°$ C. to about $4°$ C. Generally, cell permeabilizations carried out at lower temperatures are preferred because low temperatures are more likely to inhibit the activity of degradative enzymes that might alter or damage antigenic epitopes.

As contemplated in the practice of the present invention, a suitable quantity of permeabilizing agent is an amount sufficient to achieve the desired level of cell permeability. Generally, cells contacted with relatively large quantities of permeabilizing agent over relatively long time periods will lead to more highly permeabilized cells as compared to cells contacted with smaller quantities of permeabilizing agent over relatively short time periods. Those of skill in the art can easily determine, without undue experimentation, the actual quantity of permeabilizing agent, and thus, actual level of cell permeability, required to achieve optimal reduction in background binding.

As contemplated in the practice of the present invention, permeabilized cells can be separated from permeabilizing agent by methods that are well known in the art. For example, the permeabilized cells can be pelleted by centrifugation at forces in the range of about 1,000 to about 50,000 times gravitational force ("×g"). Preferably, the mixture is centrifuged at a force of about 10,000×g. Centrifugation causes the permeabilized cells to fall out of the mixture as a pellet. The permeabilizing agent can then be easily separated from the pellet by methods that are well known in the art, such as for example, aspiration. The permeabilized cells can also be separated from the permeabilizing agent by other separation methods that are well known in the art, e.g., filtration, and the like. When filtration is employed, filters having a nominal pore size rating of about 0.8 microns are preferred.

Preferably, after permeabilization, the cells are washed in a suitable volume of an isotonic saline solution such as phosphate buffered saline (PBS). As contemplated in the practice of the present invention, a suitable volume of isotonic saline solution is an amount sufficient to remove substantially all of the permeabilizing agent from the permeabilized cells. The cells may be washed either with or without agitation. The saline solution can be separated from the washed and permeabilized cells by centrifugation at forces in the range of about 800 to about 50,000×g. Preferably, the permeabilized and washed cells are centrifuged at a force of about 10,000×g. After centrifugation, the saline solution can be easily separated from the resulting pellet of cells by, for example, aspiration. The cells can also be separated from the saline solution by other separation methods that are well known in the art, e.g., filtration, and the like. When filtration is employed, filters having a nominal pore size rating of about 0.8 microns are preferred. The cells can be used immediately while wet, or optionally, the permeabilized and washed cells can be dried (e.g., by vacuum drying, air drying, lyophilization, and other like methods) and stored for later use.

As used herein, the term "lyophilized" refers to the removal of water from cells by sublimation, i.e., the direct phase transition of water in the form of ice to water vapor. Methods and equipment for lyophilization are generally well known in the art.

As contemplated in the practice of the present invention, the antibody preparation is treated with permeabilized and optionally, lyophilized cells for a period of time ranging from about 30 minutes to about 24 hours at a temperature ranging from about $4°$ C. to about $37°$ C. Preferably, the antibody preparation and permeabilized cells are contacted for a period ranging from about 30 minutes to about 5 hours at a temperature ranging from about $22°$ C. to about $37°$ C. Most preferably, the antibody preparation is treated with permeabilized cells for a period ranging from about 30 minutes to about 1 hour at a temperature ranging from about $22°$ C. to about $37°$ C. Those of skill in the art can easily determine, without undue experimentation, the most cost effective combination of variables, such as time, temperature, and volume ratio of antibody preparation to cells, to achieve optimal reduction in background binding. Generally, the antibody preparation is treated with permeabilized cells for longer periods at lower temperatures and for shorter periods at higher temperatures. For example, the antibody preparation can be treated with permeabilized cells for about 30 minutes at about $37°$ C., about 1 hour at about $22°$ C. (approximately room temperature), and about 16 hours at about $4°$ C.

After the antibody preparation has been treated with permeabilized cells for a sufficient time, the resulting treated antibody preparation is separated from the permeabilized cells. As used herein, the term "treated antibody preparation" refers to an antibody preparation that has been exposed to permeabilized cells as described herein. The treated antibody preparation can be separated from the permeabilized cells by centrifugation at forces in the range of about 800 to about 50,000×g. Preferably, the treated antibody preparation is separated from the permeabilized cells by centrifugation at a force of about 10,000×g. After the cells have been pelleted by centrifugation, the supernatant, which contains the treated antibody preparation, can be easily separated from the cells by, for example, aspiration. The treated antibody preparation can also be separated from the permeabilized cells by other separation methods that are well known in the art, e.g., filtration, and the like. When filtration is employed, filters having a nominal pore size rating of about 0.8 microns are preferred.

In accordance with another embodiment of the present invention, there is provided a method for reducing background binding in an antibody preparation having unwanted affinity for intracellular protein(s) comprising:

(i) permeabilizing optionally immobilized whole cells by contacting the whole cells with a suitable permeabilizing agent, wherein said permeabilizing agent comprises an agent selected from the group consisting of alcohols and aqueous alcohols, aldehydes and aqueous aldehydes, ketones and aqueous ketones, nonionic surfactants and aqueous media containing nonionic surfactants, and combinations of any two or more thereof, provided, however, that the permeabilizing agent is not neat acetone;

(ii) optionally lyophilizing the permeabilized whole cells;

(iii) treating said antibody preparation with said optionally lyophilized, permeabilized whole cells to produce a treated antibody preparation; then (iv) separating the treated antibody preparation from the permeabilized cells.

As contemplated by the present invention, the permeabilized cells can optionally be immobilized on a solid support. Suitable solid supports are made from either polymeric organic or inorganic materials. For example, the solid support can be made from inorganic materials such as glass or ceramic materials. The solid support can also be made from natural or synthetic polymeric materials. Exemplary natural polymeric materials include polysaccharides such as dextran, cellulose, agarose, and the like. Exemplary synthetic polymeric materials include polyamides, copolymers of polystyrene and divinylbenzene, polyacrylates, poly (vinyl alcohol), hydroxylated polyethers, and the like.

Solid supports employed in the practice of the present invention can take a variety of shapes, including column packing material, a bead, membrane, test tube, centrifugation tube, vial, multi-well plate, tissue culture dish/flask, multichambered slide, and the like.

Cells frequently can be immobilized on a solid support without the use of additional reagents. However, cell attachment can be promoted by coating the solid support with reagents such as extracellular matrix proteins. Exemplary extracellular matrix proteins suitable for immobilizing cells to a solid support include collagen, laminin, fibronectin, complex matrix proteins (e.g. lung and liver matrix proteins, and the like), and the like, as well as combinations of any two or more thereof. Cell attachment can also be promoted by chemically modifying the solid support to add a charge to the surface of the support. For example, cells are known to have an affinity for negative charges. As contemplated in the practice of the present invention, the solid support can be modified by the application of polyelectrolytes to the surface of the support, chemical derivatization of the solid support, and other methods for modifying the surface chemistry of solids as are well known in the art. Also contemplated by the present invention is the use of both reagent and surface modification of the solid support to facilitate immobilization. As contemplated by the present invention, cells can be permeabilized either before or after immobilization.

It has been discovered that the treated antibody preparations produced by the present invention are substantially free of background binding. An antibody preparation that is substantially free of background binding can be characterized by both qualitative and quantitative methods. A qualitative determination of background binding can be made from antibody binding experiments (employing cells) by using standard microscopic detection systems. In one such experiment, the antibody preparation of interest is used in undiluted form to bind to cells that are known not to express the antigen to which the antibody was raised. Background binding can be quantified by measuring, for example, a fluorescent signal from cell antibody binding experiments using Fluorescence Activated Cell Sorter (FACS) analysis.

Substantially background-free antibody preparations exhibit at least a ten-fold reduction in background binding as indicated by a change in binding signal of the antibody preparation measured before and after treatment with permeabilized cells. Preferably, substantially background-free antibody preparations of the present invention exhibit about a ten to one thousand-fold reduction in background binding after treatment with permeabilized cells. Antibody preparations are considered to be "free" of background binding if no binding signal is observed after incubating the antibody preparation, in undiluted form, with cells that do not produce the antigen against which the antibody preparation was raised.

As a specific example, substantially background free anti-luciferase polyclonal antibody preparation can be prepared by treating commercially available anti-luciferase polyclonal antibody preparation with methanol permeabilized pig hepatocytes. The treated anti-luciferase polyclonal antibody preparations have reduced background levels that are at least about ten to one thousand-fold lower than background levels in commercially available anti-luciferase polyclonal antibody preparations. Typically, anti-luciferase polyclonal antibody preparations treated in accordance with the invention are free of background binding and exhibit no visible binding signals in cells that have not been transfected with the gene encoding luciferase. This large reduction in background binding suggests that the configuration of intracellular proteins within the permeabilized cells used to remove the unwanted background binding, described herein, is not substantially altered by the permeabilization process (i.e., there is no substantial level of protein denaturation).

In yet another embodiment of the present invention, there are provided reagents for reducing the level of background binding in an antibody preparation. Invention reagents comprise immobilized, lyophilized, permeabilized whole cells, wherein said cells contain intracellular protein(s) that are not substantially denatured. The reagents contemplated by the present invention are effective at reducing the level of background binding in antibody preparations.

The invention will now be described in greater detail with reference to the following non-limiting examples.

EXAMPLE I

Isolation of Pig Hepatocytes

Hepatocytes were harvested by a two-step ethylenediaminetetraacetic acid ('EDTA')/collagenase liver perfusion. All hepatocyte isolations were performed between 11 a.m. and noon. Non-fasted animals were premedicated with intramuscular acepromazine (0.6 mg/kg), ketamine (20 mg/kg), and atropine (0.05 mg/kg), endotracheally intubated, and anesthetized using 1–2% isoflurane. The abdomen was entered through a midline incision, the hepatoduodenal ligament was dissected, and all its structures were ligated and divided, except for the portal vein, which was cannulated with silicone tubing (Masterflex, Cole-Palmer, Chicago, Ill.). Heparin (100 I.U./kg) was injected intravenously. The liver first was perfused with prewashing EDTA solution at room temperature at a flow rate of 300 milliliters ('ml') per minute by means of a roller pump (Masterflex; Cole-Palmer, Chicago, Ill.). Perfusion was initiated in situ and then continued for 10 minutes in a sterile stainless steel basin. Next, the basin was filled with the collagenase solution, which was recirculated through the liver at 300 ml per minute after passage through gas permeable silicone tubing (Silastic, Dow Corning, Midland, Mich.) submerged in an oxygen saturated water bath at 40° C. Twenty minutes later, the liver capsule was disrupted and the digested liver parenchyma was suspended in about 300 ml of ice cold 10% Bovine Calf Serum-Dulbecco's Modified Eagle Medium (BCS-DMEM). (Morsiani et al., *ASAIO J.* 42:2 155 (April–June 1995), incorporated herein by reference).

For cell filtration, a custom made stainless steel chamber was used. The chamber was designed to allow rapid cell filtration and release from the digested liver within a closed sterile system. The inner volume of the chamber is 5 liters, divided into 4 compartments by 3 stainless steel meshes of decreased porosity (i.e. 400, 280, and 100 Lancaster; Tetko Inc., Lancaster, N.Y.). The chamber was attached to the platform of a Red Rocker orbital shaker (Hoefer Scientific Instrument Inc., San Francisco, Calif.). The primary cell suspension was loaded into the chamber, after which 500 ml of ice cold 10% DMEM flushed the cells by gravity into the upper compartment of the chamber, while the platform rotated at 60 oscillations per minute. Within 1 to 2 minutes, approximately 1 liter of the cell filtrate was collected into a 1 liter disposable plastic transfer bag, which was maintained on ice.

Next, a COBE 2991 blood cell processor (COBE, Blood Component Technology, Lakewood, Colo.) was used for automated washing and purification of the liver cells. The instrument consists of a centrifuge bowl with a flexible membrane at the bottom, into which fits a sealed doughnut-shaped, disposable plastic bag. The flexible membrane is connected to a hydraulic pump that allows a liquid to be removed from the processing bag. At the hub of the bag, a rotating seal allows both filling and emptying of the bag as the bag spins. The centrifuge bowl of the cell washer was refrigerated by an air conditioning unit attached to the side of the instrument.

The filtered cell suspension was introduced into the centrifuge bag, and air was removed from the bag. Centrifugation was carried out at 600 revolutions per minute (50×g) for 2 minutes, and the collagenase solution then was removed at a rate of 350 ml per minute. Hepatocytes were washed twice with approximately 630 ml of ice cold 10% BCS-DMEM using the cell processor. Pelleted hepatocytes then were resuspended in 10% BCS-DMEM.

EXAMPLE II

Permeabilization of Pig Hepatocytes with Methanol

The pig hepatocyte suspension prepared as described in Example I was placed in a disposable conical test tube and centrifuged at 1000×g for 5 minutes at room temperature to pellet the cells. The supernatant was discarded and the cells gently resuspended in a 2:1 volume ratio of ice-cold methanol to cells. The cell suspension was rocked on a test tube shaker for 30 minutes. The suspension was then centrifuged at 10,000×g for 5 minutes. The methanol was removed by aspiration and the cells were washed three times with a 4:1 volume ratio of phosphate buffered saline (PBS) and then pelleted by centrifugation at 1000×g for 5 minutes at room temperature.

Example III

Preparation of Treated Anti-Luciferase Polyclonal

A stock 1 mg (total protein)/ml solution of an IgG fraction containing the rabbit polyclonal antibody anti-luciferase (Cortex Biochem, San Leandro, Calif.) was diluted by a factor of 1:50 in 0.25% Bovine Serum Albumin/PBS.

The anti-luciferase dilution was added to the washed methanol-treated cell pellet prepared according to Example II in a volume ratio of 4:1 (anti-luciferase solution:cells). The mixture was gently rocked on an Adams nutator (Clay Adams, Division of Becton Dickinson and Co., Parsippany, N.J.) for 20 hours at 4° C. The cells were pelleted by centrifugation at 10,000×g for 5 minutes at room temperature. The antibody suspension was aspirated from the cells, then filtered through a 0.8 micron Acrodisco® Supor® (polyether sulfone) (Gelman Sciences, Ann Arbor, Mich.).

EXAMPLE IV

Preparation of Lyophilized and Permeabilized Pig Hepatocytes and Treatment of Anti-Luciferase Polyclonal Using Lyophilized and Permeabilized Pig Hepatocytes A pellet of permeabilized pig hepatocytes, prepared as described in Example II, is lyophilized in a Virtis lyophilizer (Virtis Company, Inc., Gardiner, N.Y.). The cell pellet is lyophilized at a temperature of −75° C. for 24 hours. The lyophilized cells ($1 \times 10^8$) are added to a 2% solution of the anti-luciferase polyclonal antibody preparation to be purified (Cortex Biochem, San Leandro, Calif.) in a volume ratio of 4:1 (anti-luciferase solution:cells) and rocked on a test tube shaker for 20 hours at 4° C. The cells are pelleted by centrifugation in an IEC/Micromax centrifuge (International Equipment Co., Needham Heights, Mass.) at 10,000×g for 5 minutes at room temperature. The antibody suspension is aspirated from the cells, then filtered through a 0.8 micron Acrodisc® Suporo® (polyether sulfone) filter (Gelman Sciences, Ann Arbor, Mich.).

EXAMPLE V

Characterization of Background Binding in Untreated Anti-Luciferase Polyclonal Pig hepatocytes were transfected with the gene encoding luciferase using the liposomal preparation, LipofectAmine® (Life Technologies, Division of Gibco BRL, Gaithersburg, Md.), according to the method suggested by the manufacturer. The transfected cells were fixed with ice-cold methanol onto 12 well plates by adding enough methanol to cover the cells. The plates were placed in a −20° C. freezer for 5 minutes. After five minutes, the plates were removed from the freezer and the fixed cells were washed twice with Phosphate Buffered Saline (PBS). The wells were blocked with enough of a 1% Bovine Serum Albumin in PBS solution to cover the cells in each well. The plates were incubated at 37° C. for 30 minutes. After 30 minutes, the fixed cells were washed twice with PBS.

Dilutions of a 1 mg/ml stock solution of untreated rabbit anti-luciferase polyclonal antibody preparation (as purchased from Cortex Biochem, San Leandro, Calif.) in 0.25% BSA-PBS were prepared according to the manufacturer's recommendation for use (i.e., 1:50, 1:100, and 1:200 dilutions). A control stock solution of 1 mg/ml of a matching irrelevant rabbit IgG antibody preparation (Jackson Immune Research, West Grove, Pa.) in 0.25% BSA-PBS was prepared. Corresponding dilutions were prepared from the stock control solution (i.e., 1:50, 1:100, and 1:200 dilutions).

One set of wells containing the fixed cells was filled with the dilutions of anti-luciferase polyclonal antibody preparation (2–3 wells/dilution). A second set of wells containing fixed cells was filled with the dilutions of control IgG antibody preparation (2-3 wells/dilution). The plates were incubated for 45 minutes at 37° C., then washed three times with rocking on an Adams nutator (Clay Adams, Division of Becton Dickinson and Co., Parsippany, N.J.) with a solution of 0.01% Tween 20 in PBS.

A 1:200 dilution of a 1 mg (total protein)/ml donkey anti-rabbit-FITC conjugated F(ab')$_2$ labelled secondary antibody (Jackson ImmunoResearch, West Grove, Pa.) in BSA-PBS was prepared. The diluted secondary antibody solution was added to the all of the wells. The plates were then incubated for 45 minutes at 37° C. on the nutator. Following incubation, the cells were washed three times with rocking on the nutator at room temperature with the 0.01 Tween 20 in PBS solution (5 minutes/wash). The cells were then washed once with PBS for 5 minutes, then stored at 4° C. in fresh PBS.

The fluorescent signal in each well was measured visually using an Olympus BH2 fluorescent microscope equipped with epifluorescence optics (Olympus, Olympus America Inc., San Jose, Calif.).

Visual observation of cells incubated with anti-luciferase polyclonal preparation indicated pervasive and indiscriminate fluorescent signal patterns throughout the samples. These results are consistent with the presence of a high level of background binding antibodies in commercially available anti-luciferase polyclonal preparation. It was not possible to differentiate specific anti-luciferase binding from the background.

By comparison, visual observation of the control treated cells detected no fluorescent signal. Results from the control treated cells indicated that: (1) the control irrelevant IgG antibody preparation did not contain background binding antibodies and (2) the secondary antibodies were not causing the signal in the cells incubated with anti-luciferase polyclonal.

EXAMPLE VI

Characterization of Treated Anti-Luciferase Polyclonal

Pig hepatocytes were transfected with the gene encoding luciferase using the liposomal preparation, LipofectAmine® (Life Technologies, Division of Gibco BRL, Gaithersburg, Md.), according to the method suggested by the manufacturer. The transfected cells were fixed with ice-cold methanol onto 12 well plates by adding enough methanol to cover the cells. The plates were placed in a −20° C. freezer for 5 minutes. After five minutes, the plates were removed from the freezer and the fixed cells were washed twice with Phosphate Buffered Saline (PBS). The wells were blocked with enough 1% Bovine Serum Albumin in PBS solution to cover the cells in each well. The plates were incubated at 37° C. for 30 minutes. The fixed cells were then washed twice with PBS.

A 1:50 dilution of a 1 mg/ml stock solution of untreated rabbit anti-luciferase polyclonal antibody preparation (as purchased from Cortex Biochem, San Leandro, Calif.) in 0.25% BSA-PBS was treated to remove background binding as described in Example III. The treated antibody preparation was used at dilutions equivalent to those of the untreated antibody preparation in Example V (i.e., 1:50, 1:100, and 1:200 dilutions). A control stock solution of 1 mg/ml of a matching irrelevant rabbit IgG antibody preparation (Jackson Immune Research, West Grove, PA) in 0.25% BSA-PBS was also prepared. Corresponding dilutions were prepared from the stock control solution (i.e., 1:50, 1:100, and 1:200 dilutions).

One set of wells containing the fixed cells was filled with the dilutions of treated anti-luciferase polyclonal antibody preparation (2-3 wells/dilution). A second set of wells containing the fixed cells was filled with the dilutions of control irrelevant IgG antibody preparation (2-3 wells/dilution). The plates were incubated for 45 minutes at 37° C., then washed three times with rocking on an Adams nutator (Clay Adams, Division of Becton Dickinson and Co., Parsippany, N.J.) with a solution of 0.01% Tween 20 in PBS (5 minutes/wash).

A 1:200 dilution of a 1 mg (total protein)/ml donkey anti-rabbit-FITC conjugated F(ab')$_2$ labelled secondary antibody (Jackson ImmunoResearch, West Grove, Pa.) in BSA-PBS was prepared. The diluted secondary antibody solution was added to the all of the wells. The plates were then incubated for 45 minutes at 37° C. on the nutator. Following incubation, the cells were washed three times with rocking on the nutator at room temperature with the 0.01% Tween 20 in PBS solution (5 minutes/wash). The cells were then washed once with PBS for 5 minutes, then stored at 4° C. in fresh PBS.

The fluorescent signal in each well was measured visually using an Olympus BH2 fluorescent microscope equipped with epifluorescence optics (Olympus, Olympus America Inc., San Jose, Calif.).

Visual observation of cells incubated with treated anti-luciferase polyclonal preparation, prepared as described in Example III, displayed a discrete fluorescent signal consistent with the specific binding of anti-luciferase. The pervasive and indiscriminate fluorescent signal patterns observed with untreated anti-luciferase (as described in Example V) was notably absent. The control did not exhibit any fluorescent signals.

These results demonstrate that the treatment of anti-luciferase polyclonal in Example III was effective at significantly reducing the level of background binding without also removing the desired specific binding of anti-luciferase.

While the invention has been described in detail with reference to certain preferred embodiments thereof, it will be understood that modifications and variations are within the spirit and scope of that which is described and claimed.

That which is claimed is:

1. A method for reducing background binding in an antibody preparation having unwanted affinity for intracellular protein(s), said method comprising:
   (i) treating said antibody preparation with permeabilized cells to produce a treated antibody preparation,
      wherein said permeabilized cells are prepared by contacting whole cells with a suitable permeabilizing agent,
      wherein said permeabilizing agent comprises an agent selected from the group consisting of alcohols and aqueous alcohols, aldehydes and aqueous aldehydes, ketones and aqueous ketones, nonionic surfactants and aqueous media containing nonionic surfactants, and combinations of any two or more thereof, provided, however, that the permeabilizing agent is not neat acetone; then
   (ii) separating said treated antibody preparation from said permeabilized cells.

2. The method according to claim 1, wherein said alcohol is selected from methanol, ethanol, or mixtures thereof.

3. The method according to claim 1, wherein said aldehyde is selected from formalin, glutaraldehyde, or mixtures thereof.

4. The method according to claim 1, wherein said ketone is selected from acetone, methyl ethyl ketone, 3-pentanone, or mixtures thereof.

5. The method according to claim 1, wherein said nonionic surfactant is selected from a polyethoxylated alcohols, polyethoxylated alkylphenol, polyethoxylated fatty acid, polyalkylene oxide block copolymer, carboxylic acid ester, carboxylic amide, or combinations of any two or more thereof.

6. The method according to claim 1, wherein said whole cells are contacted with said permeabilizing agent for a period ranging from about 1 minute to about 36 hours at a temperature ranging from about −20° C. to about 22° C.

7. The method according to claim 1, wherein said whole cells are contacted with said permeabilizing agent for a period ranging from about 30 minutes to about 24 hours at a temperature ranging from about −20° C. to 22° C.

8. The method according to claim 1, wherein said whole cells are contacted with said permeabilizing agent for a period ranging from about 15 minutes to about 30 minutes at a temperature ranging from about −20° C. to about 4° C.

9. The method according to claim 1, wherein said whole cells are selected from hepatocytes, epithelial cells, mesenchymal cells, endothelial cells, muscle cells, neural cells, glial cells and combinations of any two or more thereof.

10. The method according to claim 9, wherein said whole cells are hepatocytes.

11. The method according to claim 9, wherein said whole cells are epithelial cells.

12. The method according to claim 9, wherein said whole cells are mesenchymal cells.

13. The method according to claim 9, wherein said whole cells are endothelial cells.

14. The method according to claim 9, wherein said whole cells are neural cells.

15. The method according to claim 9, wherein said whole cells are glial cells.

16. The method according to claim 1, wherein said antibody preparation is polyclonal.

17. The method according to claim 16, wherein said polyclonal antibody is raised against luciferase.

18. The method according to claim 16, wherein said polyclonal antibody is raised in an animal selected from rabbit, rat, mouse, goat, sheep, chicken, horse, donkey, or guinea pig.

19. The method according to claim 18, wherein said animal is rabbit.

20. The method according to claim 1, wherein said intracellular protein(s) are cytoskeletal protein(s).

21. The method according to claim 1, wherein said permeabilized cells are lyophilized prior to treating said antibody preparation.

22. The method according to claim 1, wherein said permeabilized cells are immobilized on a solid support.

23. The method according to claim 22, wherein said support comprises a polymeric organic or inorganic material.

24. The method according to claim 22, wherein said support is disposed in the shape of column packing material, a bead, membrane, test tube, centrifugation tube, vial, multiwell plate, tissue culture dish/flask, or multichambered slide.

25. The method according to claim 1, wherein said antibody preparation is treated with said permeabilized cells for a period ranging from about 30 minutes to about 24 hours at a temperature ranging from about 40° C. to about 37° C.

26. The method according to claim 1, wherein said antibody preparation is treated with said permeabilized cells for a period ranging from about 30 minutes to about 5 hours at a temperature ranging from about 22° C. to about 37° C.

27. The method according to claim 1, wherein said antibody preparation is treated with said permeabilized cells for a period ranging from about 30 minutes to 1 hour at a temperature ranging from about 22° C. to 37° C.

28. A method for reducing background binding in an antibody preparation comprising antibodies having unwanted affinity for intracellular protein(s), said method comprising:

(i) permeabilizing optionally immobilized whole cells by contacting the whole cells with a suitable permeabilizing agent, wherein said permeabilizing agent comprises an agent selected from the group consisting of alcohols and aqueous alcohols, aldehydes and aqueous aldehydes, ketones and aqueous ketones, nonionic surfactants and aqueous media containing nonionic surfactants, and combinations of any two or more thereof, provided, however, that the permeabilizing agent is not neat acetone;

(ii) removing the permeabilizing agent from the permeabilized, and optionally immobilized cells;

(iii) lyophilizing the permeabilized, and optionally immobilized whole cells;

(iv) treating said antibody preparation with said lyophilized, permeabilized, and optionally immobilized whole cells to produce a treated antibody preparation; then (v) separating said treated antibody preparation from said lyophilized, permeabilized, and optionally immobilized whole cells.

29. The method according to claim 28, wherein said antibody preparation is treated with said lyophilized, permeabilized, and optionally immobilized cells for a period ranging from about 30 minutes to about 24 hours at a temperature ranging from about 4° C. to about 37° C.

30. The method according to claim 28, wherein said antibody preparation is treated with said lyophilized, permeabilized, and optionally immobilized cells for a period ranging from about 30 minutes to about 5 hours at a temperature ranging from about 22° C. to about 37° C.

31. The method according to claim 28, wherein said antibody preparation is treated with said lyophilized, permeabilized, and optionally immobilized cells for a period ranging from about 30 minutes to about 1 hour at a temperature ranging from about 22° C. to about 37° C.

32. A treated anti-luciferase polyclonal antibody preparation prepared according to the method of claim 1, wherein said treated anti-luciferase polyclonal antibody preparation is substantially free of background binding due to intracellular proteins.

33. An anti-luciferase polyclonal antibody preparation, wherein said anti-luciferase polyclonal antibody preparation is substantially free of background binding due to intracellular protein(s).

34. A reagent comprising immobilized, lyophilized, permeabilized whole cells, wherein the intracellular protein(s) of said cells are not substantially denatured, and wherein said whole cells are from a vertebrate species.

35. The reagent of claim 34, wherein said cells are immobilized on a solid support.

* * * * *